United States Patent

Jackson

Patent Number: 5,417,671
Date of Patent: May 23, 1995

[54] MEDICAL DEVICES HAVING LOCAL ANESTHETIC EFFECT AND METHODS OF THEIR MANUFACTURE

[76] Inventor: Richard R. Jackson, One Atlantic Ave., Swampscott, Mass. 01907

[21] Appl. No.: 126,970

[22] Filed: Sep. 24, 1993

Related U.S. Application Data

[63] Continuation-in-part of Ser. No. 527,593, May 23, 1990, Pat. No. 5,279,594.

[51] Int. Cl.$^6$ ............................................. A61M 5/32
[52] U.S. Cl. .................................... 604/265; 604/93; 623/12
[58] Field of Search ................................ 604/96–103, 604/111, 112, 209, 264, 280, 265; 623/1, 12

[56] References Cited

U.S. PATENT DOCUMENTS

| | | | |
|---|---|---|---|
| 3,610,247 | 10/1971 | Jackson | 604/265 |
| 4,994,047 | 2/1991 | Walker et al. | 604/265 |
| 5,279,594 | 1/1994 | Jackson | 604/265 |

*Primary Examiner*—C. Fred Rosenbaum
*Assistant Examiner*—Chalin Smith
*Attorney, Agent, or Firm*—Fish & Richardson

[57] ABSTRACT

A compound with topical anesthetic and plasticizing properties is dissolved in polymeric material of a medical device. Extrusion, co-extrusion and coating techniques to form endotracheal tubes, drainage tubes and other medical devices with the topical anesthetic are disclosed. A hydrophobic anesthetic compound such as the base form of lidocaine is used which is more soluble in the polymeric wall material of the tube than in water. As a result, the anesthetic compound is transferred only to the contiguous tissue of the body passage and not disseminated systemically through the aqueous fluids. The anesthetic compound diffuses to the surface of body tissue touched by the tube where its anesthetic effect suppresses discomfort and undesired rejection reactions. Since the anesthetic compound is thus dispensed only to the contiguous tissue of the body passage, the quantity of anesthetic stored is sufficient to maintain effective anesthesia for hours or days, and undesired effects of a general dissemination through the body are avoided. Prilocaine base and dibucaine base are also used in examples. A water soluble form of topical anesthetic, achievable by reacting anesthetic base dissolved in the polymer, is provided, e.g. at an exposed surface, to enable rapid onset of anesthesia. Balloons, films and extruded cross sections are shown. Barrier and metering layers are shown to control the direction and rate of application of the anesthetic. Methods of introduction of the anesthetic into solution in the polymer are disclosed.

48 Claims, 5 Drawing Sheets

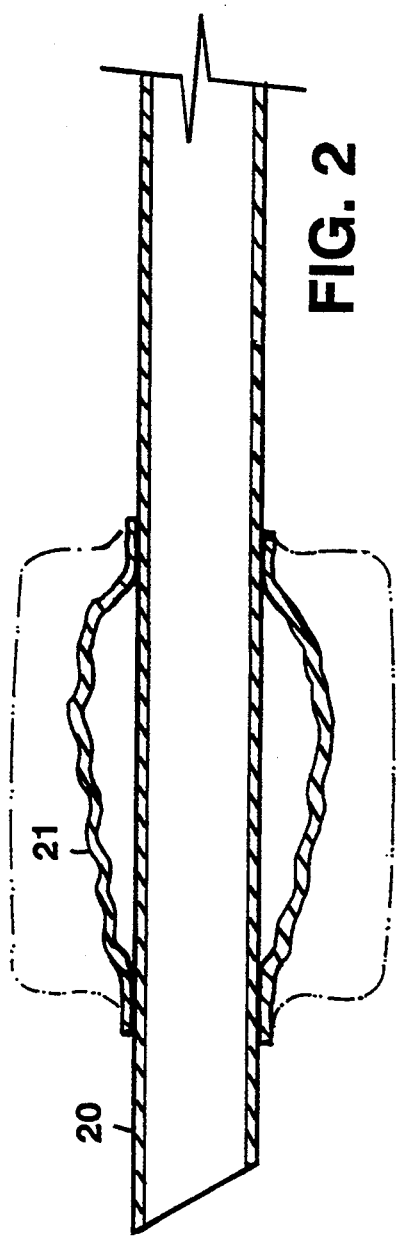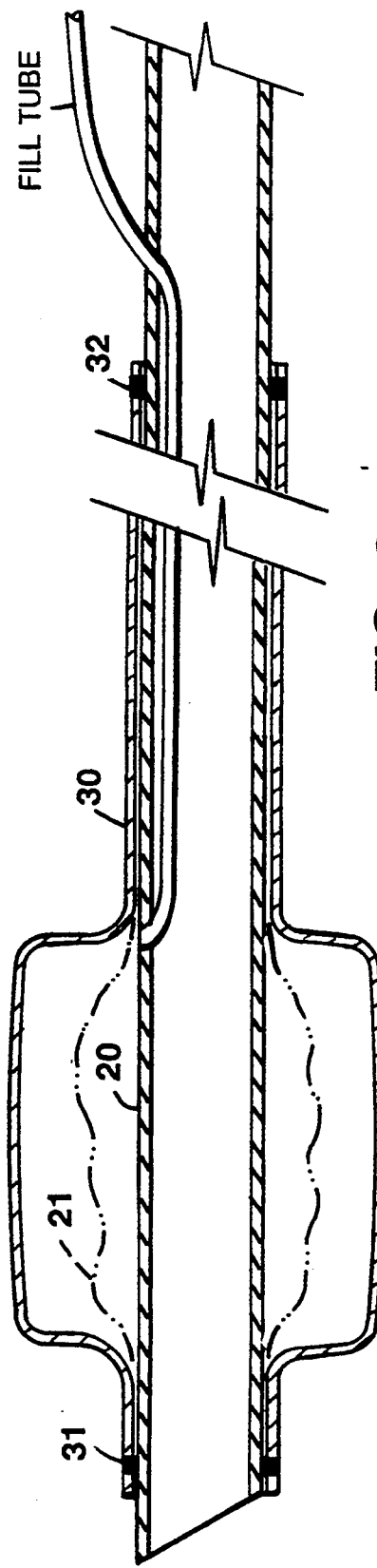

MEDICAL DEVICES HAVING LOCAL ANESTHETIC EFFECT AND METHODS OF THEIR MANUFACTURE

This application is a continuation-in-part of Ser. No. 07/527,593, filed May 23, 1990, now U.S. Pat. No. 5,279,594.

SUMMARY OF THE INVENTION

The invention relates to intubation devices which are introduced into body passages of human and non-human animals in certain medical procedures. More generally, it relates to medical devices that have a local anesthetizing effect and to methods of their manufacture.

When conventional intubation devices are introduced into body passages in connection with medical procedures they cause discomfort and often elicit ejection reactions such as coughing or gagging by the patient which interfere with the procedure and may be injurious to the patient. An object of the invention is to provide in an intubation device a tube which dispenses a topical anesthetic to contiguous tissue in the body passage to reduce or eliminate the discomfort and undesired reactions.

In accordance with one aspect of the invention, I have discovered that topical anesthetics in base form, in their own right, are potent, soluble plasticizers for polyvinyl and similar resins, and in fact, are useful as a substitute for part of the necessary plasticizer or even by themselves without the addition of other plasticizers, to produce flexible medical devices that have desired local anesthetizing effect.

According to another aspect of the invention, such a topical anesthetic with plasticizer properties is incorporated in the polymeric material making up the wall of a tube or other medical device in appropriate balance with any other plasticizer being employed to produce a product having desirable flexible properties and shelf life.

In certain preferred embodiments the anesthetic is present in solution throughout the wall thickness of the tube or device, while in other instances it is present in solution in a flexible layer or coating on the device. In the latter case, a barrier or other provision may deter diffusion of the anesthetic into the underlying body.

While the tube, for instance, is in place within a body passage, the anesthetic compound diffuses to the surface of body tissue touched by the tube where its anesthetic effect suppresses discomfort and undesired rejection reactions. The base form of anesthetic compound employed according to the invention is hydrophobic, which is more soluble in the polymeric wall material of the tube than in water. Because of the hydrophobic properties, a quantity of anesthetic compound can be stored in solution in the polymeric wall material of the tube and this stored anesthetic compound is not washed out by the aqueous fluid which is present in the body passage. As a result, the anesthetic compound is transferred only to the contiguous tissue of the body passage and not disseminated systemically through the aqueous fluids. Since the anesthetic compound is thus dispensed only to the contiguous tissue of the body passage, the quantity of anesthetic compound stored in the tube wall is sufficient to maintain effective anesthesia of the body passage for hours or days, and undesired effects of a general dissemination through the body are avoided.

Advantage of the invention however can also be taken in cases where the water-soluble form of the anesthetic is desired, e.g. for rapid dissemination from the outer surface of the tube. In this case the base form of the anesthetic, e.g. lidocaine, is initially dissolved in the vinyl of a tube or a coating on the tube to achieve uniform distribution, and subsequently a post treatment with e.g. hydrochloric acid, is employed to convert the anesthetic, e.g. all of it or a part of it nearest the surface, to the water soluble hydrochloride form, which is capable of being rapidly mobilized upon contact with body fluids.

In one particular aspect, the invention features a tube for introduction into a body passage of an animal for medical purposes. The inner surface of the tube has a wall which defines an interior lumen, while the outward facing surface of the wall contacts the body tissue of an animal upon placement of the tube in a body passage of the animal. Dissolved into the polymeric wall material of the tube is a topical anesthetic compound which is more soluble in the wall material than in water and which is at an appropriate concentration, in balance with other constituents of the wall material, such that it contributes as plasticizer to render the wall material flexible to a predetermined desired degree while being in concentration such that diffusion of the compound to a surface of the body passage in contact with the tube is at a rate effective to maintain anesthesia.

Preferred embodiments have one or a number of additional features.

The topical anesthetic compound is unreactive with ethylene oxide as used in sterilizing procedures.

The wall of the tube is composed entirely of a single polymeric material which may be a polyvinyl chloride polymer or a vinyl-urethane copolymer.

The topical anesthetic dissolved in the polyvinyl chloride tube is lidocaine base or prilocaine base, though in certain instances dibucaine base or other anesthetics of this class or mixtures thereof can be employed; the topical anesthetic dissolved in the tube made of a vinyl-urethane copolymer may be similarly selected.

According to another aspect of the invention, a flexible tube for introduction into a body passage of an animal for medical purposes is provided, the tube having a wall with an inner surface defining an interior lumen, the wall having an outward facing surface which, when the tube is emplaced in a body passage of an animal, contacts body tissue of the animal, the wall of the tube being composed of wall material having dissolved therein a topical anesthetic compound, the topical anesthetic compound being more soluble in the wall material than in water, the concentration of anesthetic compound in the wall material being such that it contributes as plasticizer to render the wall material flexible to a predetermined desired degree while being in concentration such that when the tube is emplaced in and in contact with an animal's body passage, anesthetic compound diffuses to a surface of the body passage in contact with the tube at a rate to be effective in maintaining anesthesia.

Preferred embodiments have one or a number of additional features as follows.

The tube is in the form of an endotracheal tube, to which an inflatable cuff is affixed, the inflatable cuff being comprised of a thin wall material having dissolved therein a topical anesthetic compound that is more soluble in the wall material than in water.

The tube is in a form placeable into the body through the nose, preferably the tube being a naso-gastric feeding tube.

The tube is in the form of a drainage tube having drainage entry holes along a portion of the tube, preferably the tube being constructed to lie in the posterior gutter along the spine.

The tube is constructed to pass through the abdominal wall, preferably the tube being constructed to cross the peritoneum and pass through the stomach wall.

The tube is a Foley catheter, preferably a balloon on the Foley catheter being comprised of a thin wall material having dissolved therein a topical anesthetic compound that is more soluble in the wall material than in water.

A superficial portion of topical anesthetic on the tube is of water-soluble form.

The tube is of extruded form produced by the process of extruding a feed stock comprising resin and topical anesthetic soluble in the resin.

The tube is produced by the process of applying the anesthetic to a surface of a preformed tube under conditions enabling the anesthetic to enter into solution in the wall material.

The wall material of this aspect of the invention and the other aspects that follow further preferably comprise polyvinyl chloride or vinyl-urethane copolymer, and the anesthetic compound is lidocaine base, dibucaine base, prilocaine base or combinations thereof. Also in the topical anesthetic compound is unreactive with ethylene oxide as used in sterilizing procedures.

According to another aspect of the invention a medical device for introduction into a body of an animal for medical purposes is provided, comprising a plasticizable resin, the resin having a predetermined desired quantity of plasticizer chosen to determine a predetermined flexibility characteristic for the resin, the plasticizer quantity being comprised of at least about 25% topical anesthetic base soluble in the resin, the topical anesthetic base being more soluble in the resin than in water, the concentration and character of the anesthetic in the resin being such that when the medical device is emplaced in and in contact with an animal's body fluid or tissue, anesthetic compound diffuses to a surface of the device and to the fluid or tissue in contact with the device at a rate to be effective to provide a desired dosage.

In preferred embodiments of this aspect, the medical device comprises a tube having a wall defining an interior lumen, the wall having an outward facing surface which, when the tube is emplaced in a body passage of an animal, contacts body tissue of the animal, the wall of the tube being comprised of wall material having dissolved therein the topical anesthetic base.

According to another aspect of the invention a medical device is provided in the form of an inflatable member comprising a thin, flexible wall of polymeric resin, at least an outer portion of the thin, flexible wall having dissolved in the resin a topical anesthetic base that is characterized by being more soluble in the resin than in water.

In preferred embodiments the inflatable member comprises a cuff for an endotracheal tube or is in the form of an inflatable sleeve extending along the length of a medical tube or is in the form of a balloon of a Foley catheter.

In certain preferred embodiments the thin wall is comprised of multiple layers as a result of being produced by co-extrusion of differing polymeric resin compositions, at least one of the layers having the anesthetic dissolved therein.

According to another aspect of the invention a medical device is provided having at least a portion of multiple layer form as a result of being produced by coextrusion of differing polymeric resin compositions, at least one of the layers having dissolved therein a topical anesthetic base that is characterized by being more soluble in the constituent resin than in water.

In preferred embodiments of this aspect of the invention a further layer on one side of the layer in which the anesthetic is dissolved is a barrier layer comprised of a polymeric resin in which the anesthetic base is not as soluble as it is in the layer in which the anesthetic is dissolved, in certain preferred embodiments the barrier layer being comprised of polyethylene.

According to another aspect of the invention a medical device is provided having at least a polymeric resin portion of extruded form as a result of extrusion of pellets of starting resin in which an anesthetic base is dissolved.

Another aspect of the invention is a medical device having at least a polymeric portion in which prilocaine base is dissolved as a result of application of prilocaine base in liquid form to a preformed polymeric portion under conditions enabling the prilocaine to enter into solution into the resin of the preformed portion.

In another aspect a medical device is provided having at least a polymeric portion containing a water-soluble anesthetic produced by the process of treating with a reactant the polymeric portion in which anesthetic base is in solution.

In preferred embodiments of this aspect the water-soluble anesthetic is disposed in the region of an exposed surface of the device and, deeper in the portion, anesthetic base is dissolved in the constituent resin. Preferably the water soluble form of anesthetic is a hydrochloride of the anesthetic.

According to another aspect of the invention a method is provided for making an anesthetizing tube for introduction into a body passage of an animal for medical purposes, comprising the steps of fabricating a tube having dimensional specifications suitable for insertion into a body passage of an animal, the tube having a wall made of an organic polymeric wall material, dissolving into the wall material of the tube an anesthetic compound that has topical anesthetic properties and that is more soluble in the wall material than in water, the quantity of the anesthetic compound dissolved into the wall material being such that the tube has the desired mechanical specifications and when the tube is emplaced in and in contact with an animal's body passage, anesthetic compound diffuses to a surface of the body passage in contact with the tube at a rate to be effective in maintaining anesthesia.

According to another aspect of the invention a method is provided for making an anesthetizing tube for introduction into a body passage of an animal for medical purposes, comprising the steps of fabricating a tube having dimensional specifications suitable for insertion into a body passage of an animal, the tube having a wall made of an organic polymeric wall material, preparing a transfer solution of an anesthetic compound that has topical anesthetic properties and that is more soluble in the wall material than in water in a volatile transfer fluid in which the anesthetic compound is soluble, applying the transfer solution to the outer surface of the tube to form a coating thereon containing anesthetic in sufficient quantity to provide to the tube desired mechanical specifications and anesthetizing effect, and evaporating from the coating the volatile transfer fluid.

According to another aspect of the invention a method is provided for making an anesthetizing tube for introduction into a body passage of an animal for medical purposes, comprising the steps of combining particles of an organic polymeric material and an anesthetic compound that has topical anesthetic properties and that is more soluble in the wall material than in water, the anesthetic being in sufficient quantity to provide to the tube desired mechanical specifications and anesthetizing effect, the combining step including heating the polymeric material to incorporate the anesthetic compound into the polymeric particles, to form anesthetic-infused polymeric material, and extruding the anesthetic-infused polymeric material to form a tube of dimensions suitable for introduction into a body passage of an animal for medical purposes.

According to another aspect of the invention, a method is provided for making an anesthetizing tube for introduction into a body passage of an animal for medical purposes, comprising the steps of fabricating a tube having dimensional specifications suitable for insertion into a body passage of an animal, the tube having a wall made of an organic polymeric wall material, placing the tube together with a quantity of an anesthetic compound that has topical anesthetic properties and that is more soluble in the wall material than in water in a common chamber, evacuating the chamber and maintaining the chamber at elevated temperature for sufficient time to effect transfer to and dissolution into the tube of the anesthetic compound, in sufficient quantity to provide to the tube desired mechanical specifications and anesthetizing effect.

According to another aspect of the invention a method is provided for making an anesthetizing tube for introduction into a body passage of an animal for medical purposes, comprising the steps of fabricating a tube having dimensional specifications suitable for insertion into a body passage of an animal, the tube having a wall made of an organic polymeric wall material, and coating the tube with an anesthetic liquid that includes prilocaine base anesthetic either by itself or in mixtures with lidocaine base under conditions enabling the prilocaine to dissolve into the wall of the tube.

According to another aspect of the invention a method is provided for making an anesthetizing tube for introduction into a body passage of an animal for medical purposes, comprising the steps of fabricating a tube having dimensional and mechanical specifications suitable for insertion into a body passage of an animal, the tube having a wall made of an organic polymeric wall material, with anesthetic dissolved in the wall of the tube and thereafter reacting at least a portion of the anesthetic lying near the surface to form a water-soluble form of the anesthetic near the surface.

Another aspect of the invention is a medical device for introduction into a body of an animal for medical purposes, comprising a plasticizable resin, the resin having a predetermined quantity of plasticizer chosen to determine a predetermined durometer characteristic, at least part of the plasticizer serving to attain the predetermined characteristic comprises at least one topical anesthetic compound that has plasticizer properties and is more soluble in the wall material than in water, the concentration of anesthetic compound in the wall material being such that when the medical device is employed in and in contact with an animal's body tissue or fluid, anesthetic compound diffuses to a surface of the device and into the tissue or fluid at a rate to be effective to provide a desired dosage.

Preferred embodiments of this aspect have one or more further features.

The plasticizer present comprises two or more plasticizers, one of which has the characteristic of enhancing the diffusion rate through the resin of the anesthetic compound.

The anesthetic base is lidocaine and at least 25% of the plasticizer is diisooctylpthalate.

At least 25% of the plasticizer present is topical anesthetic base.

Substantially all of the plasticizer is comprised of one or more topical anesthetic bases.

According to another aspect of the invention a method is provided of preparing an anesthetic article comprising providing a vinyl polymer in particle form such as pellets or power, imbibing into the polymer particles a plasticizer comprising an anesthetic base soluble in the polymer at relatively low temperature, forming the imbibed polymer into granules or the like at higher temperature, and extruding the granules or the like to form the anesthetic article.

Preferred embodiments of this aspect have one or more of the following features.

The plasticizer comprises at least 25% topical anesthetic base.

The plasticizer is a mixture of two or more plasticizers.

The mixture comprises lidocaine and diisooctylpthalate.

Substantially all of the plasticizer is one or more topical anesthetic bases.

The invention also provides a method of administering an anesthetic comprising disposing in a communicating relationship with body tissue or body fluid a vinyl polymer, wherein the anesthetic is of base form dissolved in the polymer.

A medical article is also provided, constructed to administer anesthetic within a body comprising a plasticizable resin, the resin containing a quantity of plasticizer, wherein a substantial part of the plasticizer is topical anesthetic base that contributes anesthetic to be administered by the article.

A plasticizable resin endotracheal tube shaft is provided, wherein the shaft comprises a topical anesthetic base dissolved in the resin.

A plasticizable resin endotracheal tube cuff is also provided, wherein the inflatable cuff comprises a topical anesthetic base dissolved in the resin.

The invention also provides a plasticizable resin endotracheal tube comprising a shaft and inflatable cuff, wherein the shaft and the inflatable cuff each comprises a topical anesthetic base and wherein the concentration of the topical anesthetic base in the exposed surface of the shaft is less than the concentration of the topical anesthetic base in the exposed surface of the cuff.

Also, the invention provides a device for introduction into a body passage of an animal for medical purposes, the device being at least partially covered with a relatively loose-fitting plasticizable resin film, wherein the film comprises a topical anesthetic base dissolved in the resin of the film.

BRIEF DESCRIPTION OF THE DRAWINGS

FIG. 2 is a cross-section of an endotracheal tube with a shaft and inflatable cuff, the cuff shown deflated in solid lines.

FIG. 3 is a cross-section of an endotracheal tube with a film covering, the cuff shown inflated in solid lines.

DETAILED DESCRIPTION OF PREFERRED EMBODIMENTS

Figure 1:
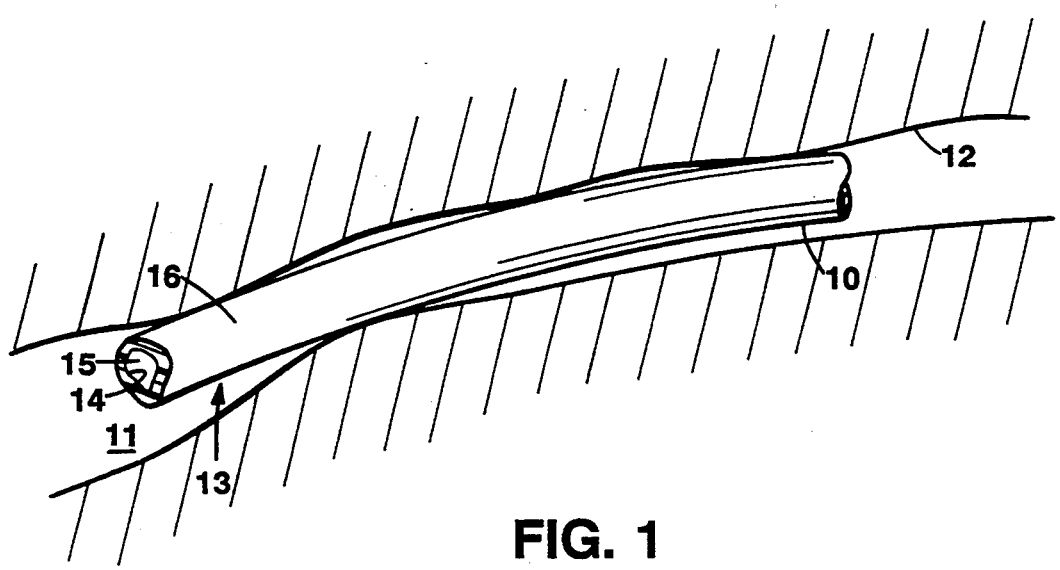
FIG. 1 shows a portion of a tube according to the invention emplaced in a body passage of an animal.
Figure 4:
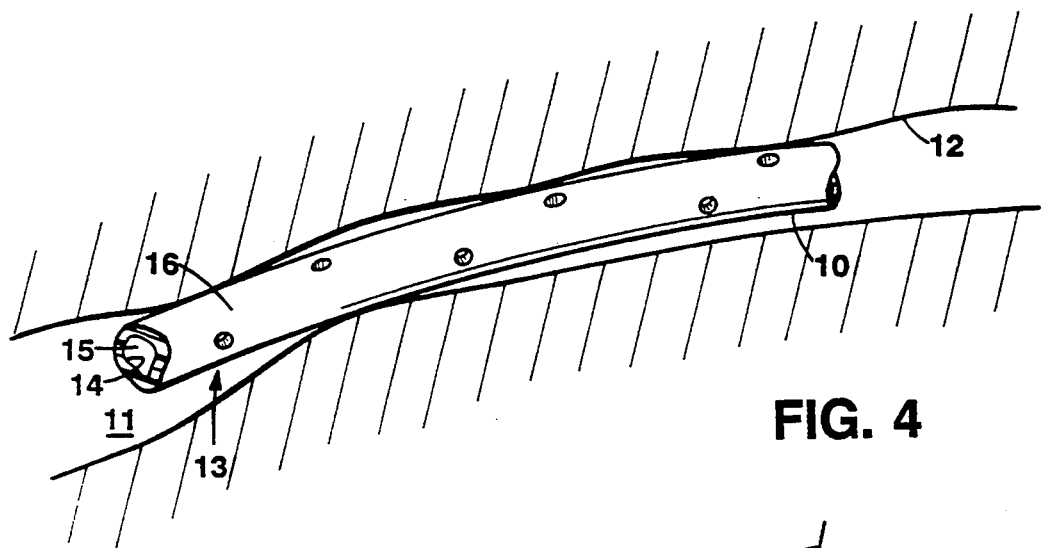
FIG. 4 is a cross-section of a drainage tube according to the invention.
Figure 5:
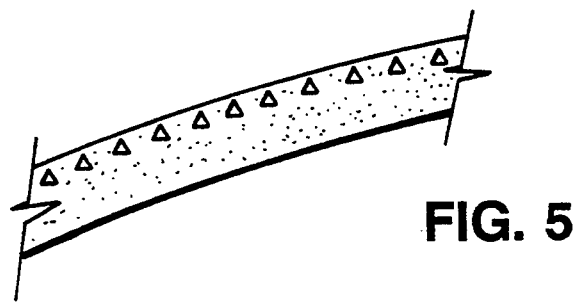
FIG. 5 is a diagrammatic partial cross-section of a further embodiment of the invention having a salt form anesthetic precipitate at an exposed surface.

As shown in FIG. 1, an intubation device including tube 13, according to the invention, is emplaced within body passage 11. Tube 13 has a wall 10 with an inner surface 14 defining lumen 15 and an outward facing surface 16 which contacts body tissue 12.

Wall 10 is composed of an organic polymeric wall material which may advantageously be polyvinyl chloride or vinyl-urethane copolymer. Dimensions of tube 13 are those conventionally used in intubation devices and may vary depending on the particular service of the device. A topical anesthetic compound is incorporated in the wall material of tube 13. The anesthetic compound is more soluble in the wall material of the tube than in water so that it will not be washed out of the wall material by aqueous fluids in the body passage. Anesthetic compounds having suitable solubilities are lidocaine base: 2(diethylamine)-N-(2,6-dimethyl-phenyl)acetamide, and dibucaine base: 2-Butoxy-N-[2-diethylamine)ethyl]-4-quinolinecarboxamide. Lidocaine is the more soluble of the two in vinyl and is usually preferred. These anesthetics found to be effective as plasticizers, in particular lidocaine, can be incorporated in vinyl powder and passed through a heated screw extruder to produce pellets that may then be used in the conventional way as a plasticized feed material for producing a coating, film or an extruded shape.

Another local anesthetic base, prilocaine, can also be used. Though stated in the Merck manual that prilocaine needles melt at 37°–38° C., I have found that in practice, prilocaine base produced by reaction of the hydrochloride form with sodium hydrate (sodium hydroxide) is liquid at room temperature. This preparation also acts by itself as an excellent plasticizer e.g. of polyvinyl chloride. It can be incorporated into vinyl powder at a lower temperature (approximately 185° F.) than that used with the other materials mentioned above. The imbibed polymer preparation can then be used as feed material e.g. to make a very fine, soft and supple, film with lasting anesthetic properties, useful, e.g., as a cuff for an endotracheal tube or as a film covering for the shaft of an endotracheal tube or other catheter.

Prilocaine, or prilocaine with dissolved lidocaine base, e.g. a eutectic mixture of about 50% to 50% proportions, in particular, can also be employed in paint-like form by application to the surface of a pre-formed product. In this case the product or its surface layer are formed with reduced plasticizer content in anticipation of the plasticizing effect of the post-applied prilocaine.

These compounds are additionally advantageous in that they are not affected by conventional sterilization techniques which involve exposure to ethylene oxide.

The method of manufacture of tubes and other devices according to the invention is illustrated in the following examples.

EXAMPLE 1

A #16 urethral catheter made of polyvinyl chloride was placed in a large glass chamber together with 10 grams of lidocaine base. The lidocaine base was contained in a watch glass physically separated from the catheter. The glass chamber was evacuated to about 0.001 mm. Hg and placed in an oven maintained for 12 hours at 77 deg C. At the end of the 12 hour period the catheter was removed from the chamber and weighed. It had not changed in appearance, but had gained 550 mg. in weight. When the catheter was held against the tongue and lips, the area of contact developed marked numbness that became evident after 5 minutes and persisted for at least 15 minutes. The catheter was then sterilized in ethylene oxide sterilant, and aerated according to a standardized hospital procedure. After this it was inserted in a patient's urethra (with substantial discomfort) and taped in place. After about 3 minutes the discomfort abated markedly, and the catheter could be move about without problem. The catheter was left in place for eight hours without discomfort. There was no pain on removal or any unusual sequela.

EXAMPLE 2

A solution of 20% dibucaine base in food grade ethyl acetate was prepared. Fifteen #7 endotracheal tubes made of polyvinyl chloride were dipped in this solution to coat the outer surfaces with the solution. The coated tubes were than baked at 77 deg C. for 12 hours to drive off the ethyl acetate and dissolve the dibucaine base into the wall material of the tubes. The tubes were then sterilized with ethylene oxide, and aerated according to standard hospital practice. The tubes emerged from the process without any change in appearance. A tube thus treated when held against the tongue for 5 minutes produced a marked numbness on the contacted areas which lasted for 45 minutes. Ten of these tubes were introduced into the trachea (wind pipe) of dogs in connection with surgical procedures. The person who performed the surgical procedures noted that when using the treated tubes there was less coughing and chewing on the endotracheal tubes than when conventional tubes were used in similar procedures, and also noted that the animals remained asleep with lower concentrations of general anesthetic agent. None of the animals suffered from any sequela that could be noted.

EXAMPLE 3

Ninety five grams of pellets of vinyl-urethane copolymer (Vythene, Dexter Chemical) and 5 grams of dibucaine base were baked at 93 deg C. for 12 hours with occasional stirring. This process incorporated the dibucaine base into the material of the pellets. Three grams of these treated pellets were further treated by pressing between two metal plates held at 171 degrees C. in vacuum to create a sheet of film about 0.25 mm thick. A sheet of film emerged that was clear, elastic, and very strong. It is believed that the pressing operation simulates the mixing and working of such pellets when they are extruded in a conventional processing for making intubation devices. A piece of this film was tested on the tongue and lips and found to have strong anesthetizing properties. Numbness started to develop in 5 minutes, peaked in intensity in 15 minutes, and persisted for at least 45 minutes. A piece of the film was soaked in 38 degree C. water for 24 hours. It is believed that this soaking procedure simulates the exposure of a tube to aqueous fluids during emplacement in a body passage. At the end of the soaking period the film was again tested on the tongue and lips and exhibited anesthetizing effects as before, but with a slower onset and somewhat diminished intensity.

EXAMPLE 4

Ten grams of lidocaine base and 90 grams of vinyl-urethane copolymer pellets were baked with agitation at 93 degrees C. for 12 hours. At the end of this treatment the pellets stuck firmly to one another. After cooling, the pellets were broken apart, and 3 grams were pressed at 171 degrees C. into a film about 0.25 mm thick. The film was clear, elastic, and tough. When a piece of this film was held on the tongue, intense numbness developed after 5 minutes and persisted for at least 15 minutes. After soaking the film in 38 degree C. water for 24 hours, a test against the tongue showed a numbing effect but at a diminished level. Two hours after the soaking, the film again had strong numbing properties.

EXAMPLE 5

A solution of 30% lidocaine base in ethyl acetate was prepared. A #14 naso-gastric tube made of polyvinyl chloride was coated by dipping in this solution. The coated tube was then baked for 12 hours at 77 degrees C. to drive off the ethyl acetate and incorporate the lidocaine base into the tube material. The tube was then passed into a subject's stomach through the nose (with substantial discomfort because of the marked sensitivity of the nose plus problems with the gag reflex). Initially after introduction of the tube, any movement of the tube caused sharp pain in the nasal passage and induced gagging. After a few minutes had passed, the tube could be manipulated without causing gagging or discomfort. The tube was taped in place, left for 12 hours, and removed without disturbing sensations. When tested later on the tongue and lips, numbing effect was still present, although in lowered intensity.

In the foregoing examples, whereas novel, desirable effects were demonstrated in useful form, it was found that the products, if not used quickly, became tacky to the touch over time, and, for some purposes, were not of acceptable quality or stiffness. The starting polymer pellets or tubes in each case contained usual quantities of plasticizer, as is common in making vinyl products and the like.

It has been further discovered that the anesthetic base has an unexpectedly strong plasticizing effect which combined with the already-present plasticizers in conventional wall materials, can constitute an over-load of plasticizer. This can produce, over time, objectionable surface tackiness and undesirable flexibility. It has been found, however, that by considering the anesthetic base as a plasticizer and by then reducing the total plasticizer content to conventional proportions taking the anesthetic base itself into account as a plasticizer, a product can be produced with predetermined desired flexibility, less tackiness to the touch and with significantly improved shelf life. This discovery has led to products with significantly improved commercial features.

EXAMPLE 6

In an experiment to demonstrate the plasticizing effect of a local anesthetic in base form, vinyl film was pressed effectively with 40% lidocaine base and 60% non-plasticized polyvinyl chloride without addition of any other plasticizer. At a relatively low temperature, about 165°–200° F., the local anesthetic base was imbibed into the polyvinyl chloride powder. Subsequently, the powder in which the lidocaine had been imbibed, was pressed at 325° F. for four minutes. The powder was transformed into a thin, continuous clear, very flexible film that has anesthetic properties, the lidocaine base being dissolved in the vinyl film.

EXAMPLE 7

Figure 11:
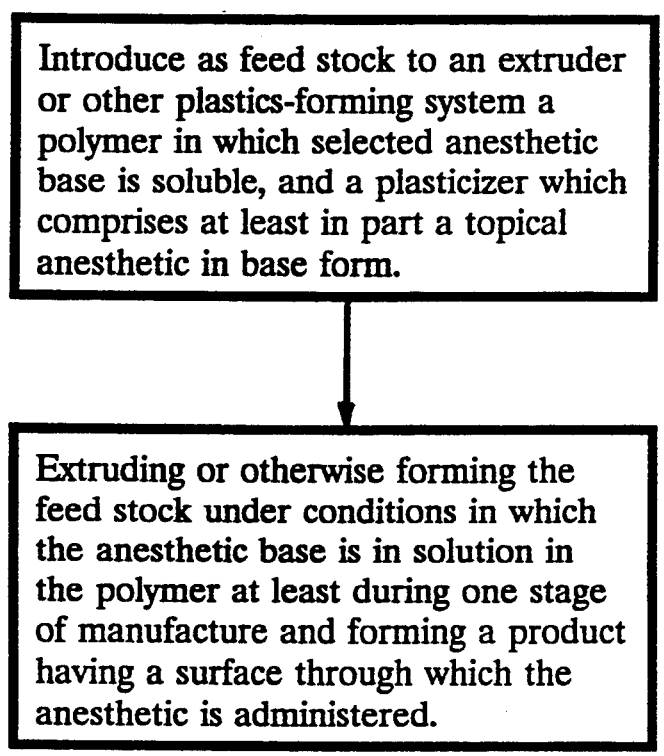
FIG. 11 and 12 are process flow diagrams illustrating steps in preferred methods of manufacturing products according to the invention.

In an analogous way, a product may be extruded. The general process employed is illustrated in FIG. 11. In a specific embodiment a non-plasticized vinyl powder is treated at the same low temperature as described in Example 6 to imbibe the lidocaine base, followed by the passage of the treated powder through an extruder to extrude it to form extruder-feed pellets. The pellets, with lidocaine now imbibed, is then used as a feed material in various forming processes, e.g. extruding vinyl tubing in the conventional way, or extruding an outer- or inner-anesthetizing layer in a co-extruded product, or forming an extruded tubular preform from which a balloon or cuff is blown or producing and applying a liquid or molten coating material upon a preformed object.

EXAMPLE 8

The observation has been made that when one uses lidocaine as the only plasticizer for polyvinyl tube at relatively reduced concentrations as may be desired in view e.g. of economic concerns, the lidocaine is not delivered to the tissue as rapidly as may be desired under some circumstances. It has been found, however, that improved performance is achieved when the anesthetic base is combined with another plasticizer, which may even be another anesthetic base, prilocaine. Thus, while one can make an effective product using e.g. 10–20% lidocaine in the absence of other plasticizers, where improved mobility of the anesthetic base is desired, it is preferred that there be present an additional plasticizer, e.g., prilocaine or IDOP (diiso-octyl phthalate) or another such conventional plasticizer or combination of plasticizers, such as ESO or adipic acid. Preferably the additional plasticizer constitutes at least about 25% of the plasticizer present, by weight, and most preferably about 50% of the total percentage of plasticizer present, though it may be greater. At least 25% of the total plasticizer by weight is preferably local anesthetic base, and as indicated, for certain applications most preferably about 50% by weight.

Particularly good results for endotracheal tubes are obtained by incorporating IDOP as the additional plasticizer. A very satisfactory ratio of total plasticizer was found to be 50% lidocaine base, 50% IDOP by weight, and employing 40 parts by weight of the combined plasticizer to 60 parts by weight polyvinyl chloride, for making a thin film having flexibility of a character useful for the inflatable cuffs of endotracheal tubes, e.g. cuff 21 of the endotracheal tube of FIG. 2.

A specific composition is in parts by weight, 100 PVC, 10 IDOP, 3 heat stabilizer, ¼ stearic acid, and 32.5 lidocaine (about 12.5% of the total weight) to produce a balloon film material of 70 durometer, suitable for use as a low pressure inflatable endotracheal cuff, with rapid anesthetic onset. For a composition of less rapid onset, the major ingredients may be present in percentages by weight, as follows: 60% PVC, 30% IDOP, and 10% lidocaine. The total composition in parts by weight may for instance be PVC 100, IDOP 30, ESO 5, stabilizer 5, and lidocaine 20, to achieve 85 durometer.

For making the shaft 20 of the endotracheal tube shown in FIG. 2, a somewhat harder composition is desired. This is attained by incorporating 10% lidocaine and 20% IDOP, by weight, with 70% polyvinylchloride.

The hardness or softness of the resulting product depends not so much on the ratio of the local anesthetic plasticizer to the other plasticizer as much as it depends on the total quantity of plasticizer present.

Since the part of the endotracheal tube that comes in intimate contact with the trachea and thus traumatizes the trachea is the flexible, inflatable cuff 21, a greater percentage of the anesthetic in certain cases is preferably used in the cuff substance to achieve a greater anesthetizing effect, while less is used in tubular shafts for reasons of economics.

EXAMPLE 9

Prilocaine base was produced by reaction of the hydrochloride form of prilocaine with sodium hydrate, to produce at Ph 11 a liquid form of the anesthetic base at room temperature. Polyvinyl chloride powder is heated to 185° F. and the prilocaine base is imbibed into solution in the polymer powder. The imbibed resin is then introduced to a pellet-forming extruder. In some examples, additional plasticizer is added and in other examples not, e.g. concentration of 30% lidocaine alone are employed. Extruder feed pellets are thereby formed. Using such pellets as feed, thin wall balloon preform tubing is extruded. Thereafter a local mid portion of a section of the preform is heated under controlled conditions and the section is introduced to a blow mold. Gas pressure is applied to blow the heated section into the form of a balloon. Inflatable balloons of the form of floppy endotracheal cuffs and of the shape of balloons for Foley catheters are effectively formed. The film of the balloons is soft and supple and is found to have lasting topical anesthetizing qualities.

EXAMPLE 10

Figure 12:
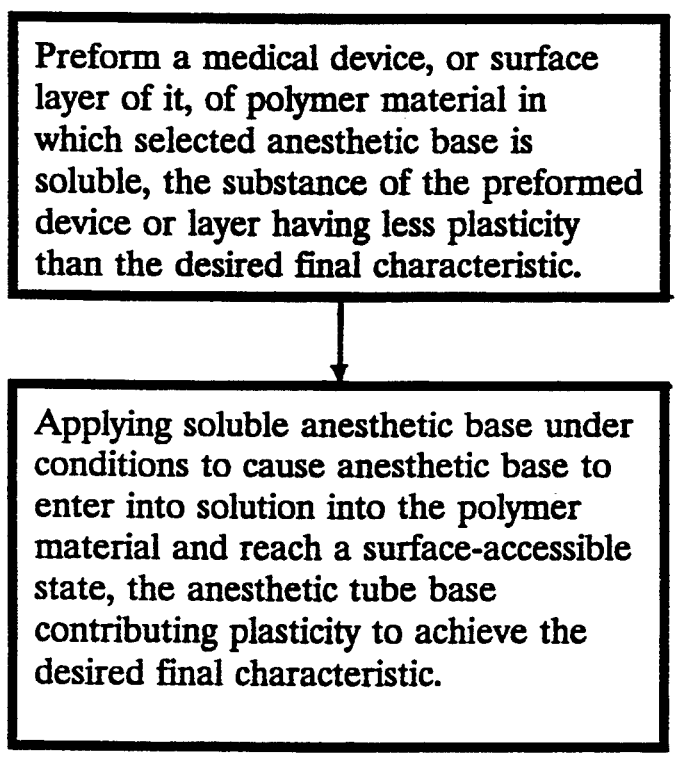

A general process by which the anesthetic base is applied as a step following formation of an article is illustrated in FIG. 12.

In a preferred embodiment, an endotracheal tube cuff of pvc is formed using standard techniques except that less plasticizer is employed from that required to meet the predetermined desired flexibility (durometer) requirements for the finished product. A controlled thickness of liquid prilocaine base is applied to the exterior of the temporarily distended cuff while the cuff is moderately heated to e.g. 165° F. to expedite diffusion of the anesthetic base into solution in the cuff material. The thus-applied anesthetic base then serves as additional plasticizer to decrease the durometer of the film to the desired predetermined value. After the coated layer has dissolved into the cuff material the cuff is applied by conventional techniques to the shaft of an endotracheal tube.

Following the same techniques other self-anesthetizing medical balloons are formed including the balloons of Foley catheters.

The resultant product produces rapid onset of topical anesthesia.

EXAMPLE 11

Endotracheal tubes made as described in examples 8, 9 and 10 are useful during surgical procedures where it is critical that the patient not cough but remain exceedingly still. An example is opthamological surgery. Any coughing during anesthesia for such a procedure is critical because if coughing occurs, the vitreous humor of the eye can be displaced.

During such an operation, it is desirable to have the anesthetizing effect of the local anesthetic delivered from the device begin at least within about 5 minutes of entubation because muscle relaxants administered before introduction of the tube into the trachea usually last five to 10 minutes before beginning to wane. After that, it is important that the patient not react to the presence of the endotracheal tube. Endotracheal tubes made according to the present invention do not cause reaction as long as the patient is in a reasonable general anesthetic state. Under these conditions the patient is found not to cough on the tube.

Presently preferred compositions for use in conditions where it is desired to have onset of the anesthetic effect occur within five minutes and taking advantage of the plasticizing effect of lidocaine are described in Examples 8, 9 and 10. Another effective device for eye surgery includes a salt form of the anesthetic, e.g. lidocaine hydrochloride, present at the immediate surface of the device, as a result of conversion of the dissolved base form anesthetic, as described later herein.

EXAMPLE 12

The invention is also useful in virtually all other surgical procedures involving endotracheal tubes. Near the end of a procedure when the anesthesiologist begins tapering off the amount of anesthesia administered to the patient and the muscle relaxants have worn off, it is a particular advantage if the attending physician is able to adjust the position or remove the endotracheal tube without causing coughing or bucking of the patient. Coughing or bucking, for instance, following procedures such as hernia repair, are likely to cause rupture of the stitches. Effective local anesthesia under these conditions is maintained by endotracheal tubes and cuffs according to this invention.

Also, it has been observed that with endotracheal cuffs and tubes containing lidocaine in solution, as have been described, persistence of numbness on the tongue lasts for only about 10 minutes after the film or tube containing the lidocaine local anesthetic has been removed. This indicates that similar numbness should persist only for this time in other tissues of the airway. Such shortness of persistence of anesthesia is desirable as it avoids problems with aspiration of vomitous that might occur due to prolonged effect of anesthesia. Prilocaine is also useful for such applications as its effect also lasts about 10 minutes, whereas some other anesthetics such as dibucaine may be less suitable for this particular application because the anesthetic effect lasts for, e.g., 45 minutes after removal of the tube.

EXAMPLE 12

For use of endotracheal tubes for patients whose breathing is supported by a respirator for prolonged periods, there are different considerations.

On a respirator, one may desire the self-anesthetizing endotracheal tube to remain in place for days rather than hours, and the lasting anesthetic effect after removal is less of a consideration. In this case, the shaft 20 of the tube itself is extruded with a large quantity of, lidocaine or dibucaine in its composition, for example, to enhance the long-term effect of the local anesthetic upon the contacted tissue.

A composition of 10% IDOP, 10% lidocaine base, and 80% vinyl, produces a tube of suitable characteristics in which the anesthetic effect lasts for one or a few days to keep the tissues numb.

A composition formulated for fast onset during administration of general anesthesia is also useful for applications requiring a longer duration of use. It is contemplated that in some instances, the same tube that is provided for general anesthesia will also be useful for patients on the respirator with resultant simplification of maintaining hospital inventory and permitting economies of bulk purchase. In a preferred embodiment of a tube for such diverse applications, it is presently preferred to employ lidocaine or prilocaine. In another preferred embodiment, the anesthetic at the surface only is of the water soluble salt form, either as a result of separate application or as a result of conversion of the base form that is present in solution near the surface, while deeper lying anesthetic is of the base form, in solution.

EXAMPLE 14

An alternative embodiment useful during surgical anesthesia, where duration of anesthetizing effect is not as important as it is for critical care patients, is illustrated in FIG. 3. The endotracheal tube is provided with a loose fitting thin sleeve 30 (not tightly adherent to the endotracheal tube). The sleeve 30, e.g. of 0.007" thickness, is extruded from the same mixture of local anesthetic, IDOP and resin as is used for the cuff 21 of FIG. 2. In this manner, one avoids the expense of including the anesthetic agent in the entire wall of the shaft of the endotracheal tube while still providing four to five hours of local anesthesia to the airway.

In this particular embodiment in a localized region, the sleeve 30 is blown to form the cuff 21 itself. As shown in FIG. 3, the sleeve 30 is bonded at both ends, 31 and 32, to the shaft 20 of the endotracheal tube, for instance, heat sealed to a vinyl tube. Similarly, in another preferred embodiment, the sleeve at the proximal end of the cuff 21 or balloon is similarly bonded to shaft 20. In use, the separate nature of the sleeve wall prevents substantial diffusion over time of the anesthetic into the vinyl wall of the tracheal tube itself, thus contributing to the shelf life of the product.

Furthermore, the smaller diameter sleeve portion proximal of the balloon as shown in FIG. 3 in use is distended by the low pressure inflation air, to provide a cushioning, protective effect to tissue and structures engaged by the endotracheal tube and ensuring good tissue contact for transfer of the anesthetic.

EXAMPLE 15

The invention has wide applicability to other types of medical tubes. One that has been tested and found to be effective is prolonged intubation of the stomach through the nose with a self-anesthetizing naso-gastric tube for keeping the stomach drained of fluids. The points of pain for a naso-gastric tube are primarily in the nose. These points may not hurt initially, but within a day or so, the nose becomes very irritated, sore and painful. Pain also develops in the back of the throat since the tube is a foreign body that causes the patient to reflexively swallow in attempt to dislodge the foreign body. Pain arising at these points can readily be alleviated according to the invention.

A conventional pre-formed naso-gastric tube dipped in the lidocaine base and ethyl acetate has been found to emerge very soft, easily kinked and somewhat difficult to insert. By reducing the amount of other plasticizer incorporated during manufacture of the tube, this detrimental result can be avoided. Thus, one starts with a stiffer, harder durometer tube prior to dipping.

Thus, a pre-formed vinyl tube formed with reduced amounts of conventional plasticizer is treated by dipping in a 25% solution of lidocaine base and ethyl acetate, following the procedure of Example 5. The patient will remain comfortable with the tube in his nose for approximately six days. In lieu of dipping, these tubes can be extruded directly using the formulation that has been described in which the anesthetic base serves as predetermined plasticizer of the vinyl resin.

EXAMPLE 16

Another application of the invention is a chest tube or other drainage tube in the body that extends through a sensitive area. In a specific example the drainage tube of outer diameter in the range of 5/16 inch to ½ inch and wall thickness of 1/16 inch has a length of 2 feet. In the distal-most 4 to 6 inches of length are provided drainage holes. For instance, in the first 4 inches of the tube 6 oval holes, with direction of elongation axially aligned, are spaced along and about this tube. By including lidocaine base in its composition, the tube becomes more readily tolerated.

Figure 6:
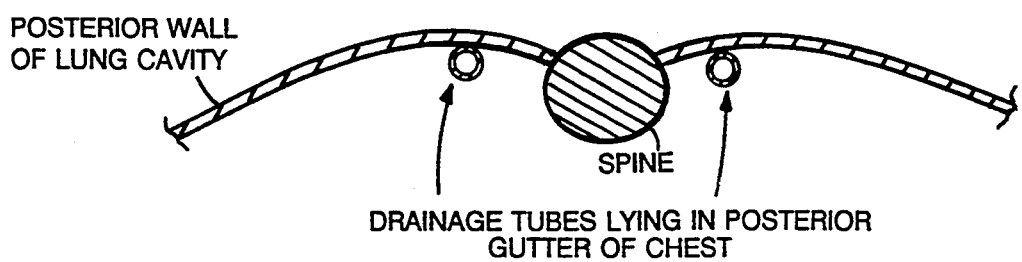
FIG. 6 is a diagrammatic illustration of a drainage tube according to the invention, placed in the posterior gutter along the spine, with its interior surface directed to the lung cavity and its exterior surface directed toward the posterior chest wall.
Figure 7:
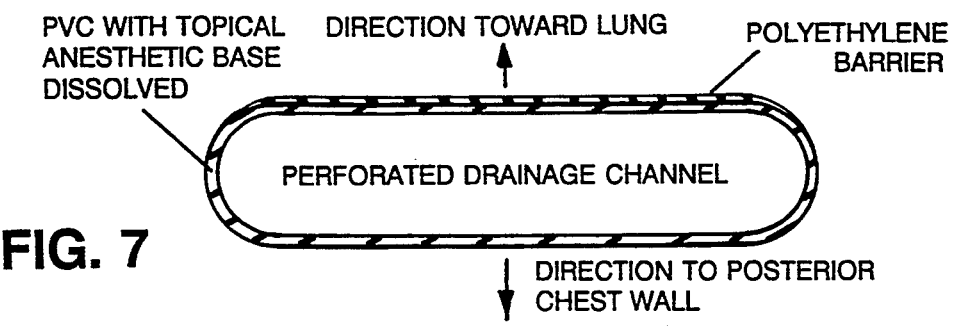
FIG. 7 is a diagrammatic illustration of a preferred flattened form of the chest tube with a barrier layer directed toward the lung cavity.

An improved chest drainage tube is shown in FIG. 6. In a thoracotomy, an opening in the chest is created between the ribs, the ribs being spread apart, through which an operative procedure is performed, usually upon the lungs. The procedure may be used when cancer of the lungs requires removal of part or all of the lung. During recuperations, these incisions are very painful in the first several days. According to this aspect of the invention, a chest tube with a large amount of local anesthetic dissolved in the tube wall or outer layer of the tube is placed in the posterior gutter of the chest. The tube is fixed next to the intercostal nerves such that topical analgesia is provided to the skin and the chest wall incision, sustained for several days for the patient.

One effect of such a tube is to relieve pain. Another is to enable drainage from the body cavity. Conventionally placed tubes that extend out of the chest wall are very irritating to the patient if moved in any way. The present invention enables patients to better tolerate the tube. The use of such tubes can thus be more frequent, with considerable benefit to patients.

EXAMPLE 17

There are also important embodiments of the invention for urology. Certain urethral catheters are currently made of vinyl. Especially for the male, a catheter that is left in the bladder is very irritating to the penis. A Foley catheter construction according to FIG. 1 or with a sleeve 30 as shown in FIG. 3 made from a composition of lidocaine base and vinyl and the catheter itself also made out of the same composition, can be held in place essentially without discomfort. The anesthetic base serves as at least partial plasticizer to reach the desired flexibility of the urethral tube as described above.

EXAMPLE 18

Local anesthetic bases (lidocaine base in particular) are very soluble in vinyl, and when coated or applied on the surface or into a surface layer of a vinyl tube tend, over time, to migrate into the deeper aspects of the tube, thereby attenuating the effect on the surface of the tube. According to a further aspect of the invention, a compatible, intermediate barrier coating, p.v.a. for example, is provided on the surface of a vinyl tube before the application of a vinyl-lidocaine coating. The p.v.a. coating serves at least as a partial diffusion barrier that prevents substantial migration of lidocaine from the surface of the tube into deeper aspects of the tube, thus enabling restriction of the total amount of lidocaine required to fabricate the tube.

EXAMPLE 19

Another feature which slows migration of local anesthetic bases into deeper aspects of vinyl tubing is accomplished by treating the lidocaine-p.v.c. coated tubing with hydrochloric acid, thereby converting the coating or a superficial portion of it to the water-soluble hydrochloride form which forms a fine precipitate in the tube wall. Since the hydrochloride is insoluble in the vinyl, it remains as a precipitate of fine particles in the treated surface region.

EXAMPLE 20

A medical tube is first formed according to one of the forms of Example 8. Then to provide a superficial distribution of the water-soluble hydrochloride form, for quick onset time, the exterior surface of the tube or cuff is treated for a suitably limited duration with hydrochloric acid vapors to convert the anesthetic base to hydrochloride form, which precipitates in the vinyl in a micro distribution at and near the surface. Such a product can combine fast onset with long duration of effective topical anesthesia.

For a tube or other article in which the salt form of the anesthetic is desired substantially below the surface, advantageously a soluble porsigen (distribution of fine soluble substance that is to be dissolved and washed away) is included in the feed stock from which the anesthetic base-laden article is extruded. Subsequently the article is treated with solvent, e.g. water, to dissolve the porsigen to form a network of pathways into the interior of the resin. The tube is then treated with acid vapor, with the pathways providing access to the acid to cause deeper lying anesthetic to be converted to the salt form. During use the deeper-lying anesthesia salt is then available to be mobilized by body fluids via the pathways.

EXAMPLE 21

Figure 8:
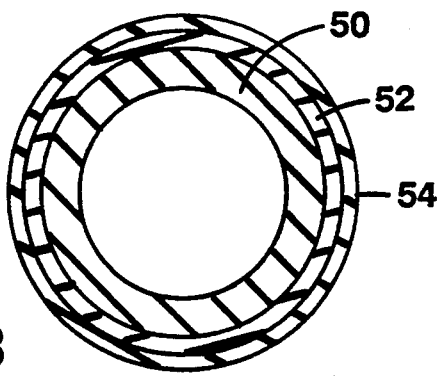
FIG. 8 is a cross-section of a tube formed according to the invention, formed by co-extrusion techniques, and having an exterior surface through which anesthetic is applied.

A tube having an anesthetic-diffusion barrier layer is formed as a coextrusion of the form shown in FIG. 8. The inner layer, constituting main body 50 of the tube, e.g. about 75% to 85% of the entire wall thickness, comprises conventionally plasticized polyvinyl chloride, and its flexibility establishes the main structural properties of the tube. Intermediate co-extrusion layer 52 comprises a compatible polymer in which the topical anesthetic is not as soluble as it is in vinyl. Selected grades of polyethylene, for instance, high density polyethylene may be employed or other polymers or copolymers of known compatibility with p.v.c. which display a slower anesthetic diffusion capability than p.v.c. Depending upon the diffusion barrier qualities of the material selected for the inner layer, or for other properties, e.g., kink resistance or passability, that such layer may be depended upon to contribute to the tube, barrier layer 52 may constitute from about 1% to about 10% or more of the total wall thickness of the coextrusion. Outer, self-anesthetizing layer 54 constituting from, e.g., about 5% to about 25% of the wall thickness, is typically p.v.c. or other resin in which anesthetic base is soluble, and it may contain only the anesthetic base as plasticizer. For example, prilocaine is either imbibed in the starting material, or painted, dipped or sprayed on as a post application process, and allowed to be imbibed and enter into solution in the tube wall. In other embodiments, e.g., in the case of lidocaine, other plasticizers may be present, to contribute to the mobility of the lidocaine, or to contribute desired flexural or other physical properties, to the exterior layer.

In certain embodiments, after fabrication, the exposed outer surface of the tube or other coextruded device may be treated, e.g. with a hydrochloric acid solution, e.g. to precipitate superficial crystals of the hydrochloride form to provide a rapid onset effect as has been described, while depending upon diffusion of the base form for long term sustaining of the topical anesthesia.

EXAMPLE 22

Figure 9:
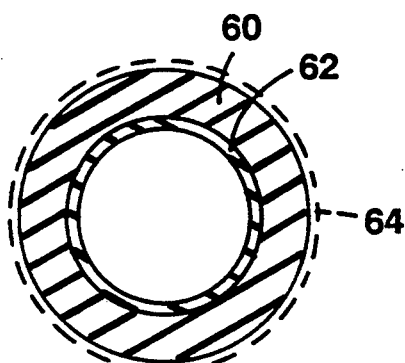
FIG. 9 is a cross-section of a further tube according to the invention in which the internal lumen is protected from dissolved anesthetic with another feature suggested by dashed lines.

The form of coextrusion shown in FIG. 9 is constructed to convey fluids to or in the body, e.g., enteral food mixtures, blood, or drug solution from a subcutaneously implace port. The outer, major thickness layer 60 of the tube comprises e.g., p.v.c. in which the topical anesthetic is in solution according to the previous examples. An internal barrier layer 62 is provided to restrict diffusion of the anesthetic to the contents of the lumen of the tube. Layer 62 may be of selected material and thickness to serve effectively as a total barrier to the migration of the anesthetic. Such construction is useful for a naso gastric or PIG enteral feeding tube to prevent introduction of the anesthetic to the nutrients. It also is useful in a drainage tube to prevent loss of anesthetic to the drainage liquid, thus to enhances the useful life of the product.

The selected material and thickness for internal layer 62 may instead be selected to serve as a metering layer to control the diffusion rate and thus the dosage of the anesthetic being introduced to the contents of the lumen, as in the case where lidocaine is to be introduced to blood or a saline solution for antiarrythmia therapy.

Thus inner layer 62 may comprise vinyl in which the anesthetic is not dissolved, but through which it can diffuse at a predetermined rate. In other instances the diffusion rate of the PVC itself is employed as a control to meter the administration of the dissolved base-form anesthetic.

In any case where the selected polymer composition is not an approved material for the duration the tube or device is to be within or exposed to fluids in or entering the body, the internal layer may be selected to have greater biocompatibility than the substance of main body layer 60.

Likewise, as suggested in dashed lines in FIG. 9, an outer coextruded layer 64 may be employed for either instoring or biocompatibility functions (or both) following the above principle. Also, in cases where the function of the tube is to deliver anesthetic to fluid within the lumen, outer layer 64 may be selected to have barrier qualities, to prevent loss or exposure of the anesthetic to surrounding tissues or fluids.

EXAMPLE 23

Figure 10:
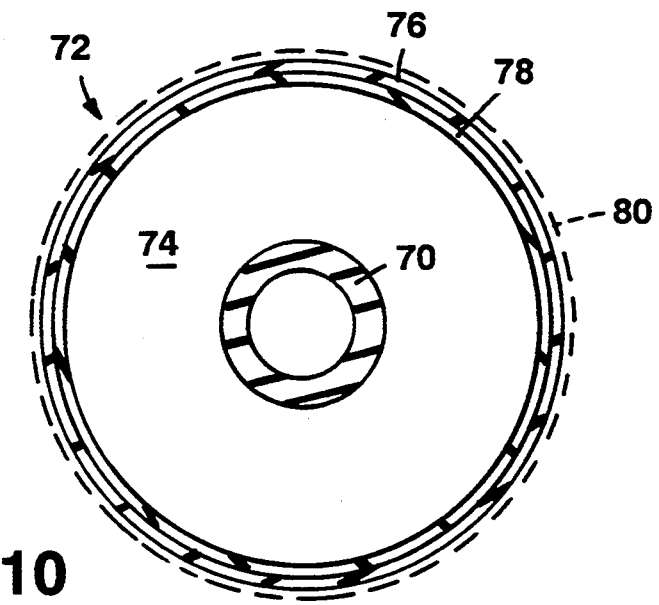
FIG. 10 is a cross-sectional of a further tube having an inflatable member according to the invention.

Referring to FIG. 10, the cross-section represents a cross-section of a balloon catheter or endotracheal tube. Inflatable balloon or cuff 72 is mounted to shaft 70. The balloon or cuff is depicted in inflated state with space 74 filled with inflation fluid which may be air or liquid, depending upon the application. It may also comprise radio-opaque contrast medium for cases of percutaneous insertion and radiographic placement.

The wall thickness of the balloon or cuff 72 is of coextrused form, as a result, e.g. of coextrusion of the preform from which the balloon or cuff is blown.

The outer layer 76 comprises the anesthetic-delivering layer and may comprise, e.g., p.v.c. formed from anesthetic imbibed feed pellets, or as a result of post-application, as by introduction of prilocaine in the liquid state or by application of the anesthetic in a carrier as has been described.

The inner layer 78 may be formed of a selected different material for providing, e.g., desired physical properties to the overall balloon, and/or to minimize the amount of anesthetic by providing barrier properties, e.g. to concentrate the anesthetic in outer regions of the cuff or balloon thickness.

As indicated in dashed lines, outermost layer 80 may also be included, e.g., for instoring or biocompatibility purpose as has been described. It can also carry a topical anesthetic, e.g., to achieve rapid onset. Thus outer layer 80 may include anesthetic in water soluble form. It may also include porsigens or the like, for instance porsigens included in p.v.c., to enable greater mobility of the anesthetic base or the hydrochloride form to the outer area, to enhance the rate of administration.

In one case the material of the inner layer (or one of a multiple number of inner layers) is non-extensible and determines a predetermined maximum diameter of the inflatable member, to serve, e.g., as a dilatation balloon. In one case such a layer is PET. In the case the resin in which the anesthetic is described is not entirely compatible with another layer, an intervening coextruded layer is provided that is compatible with the different resins on its two sides.

Other Embodiments

There are, of course, many other situations in which vinyl drainage tubes are necessary to drain puss and fluid from an abscess or from the abdomen. These tubes can be manufactured to incorporate local anesthetic in their composition following the above examples to enable the patient to be much more comfortable while entubated during the post-operative period.

In post-operative cases, the tube often protrudes through the abdominal wall. Pain is derived from sympathetic innervation of the peritoneal cavity. In addition, pain arises at the skin interface where somatic nerves transmit pain caused by easy movement of the device. PEG and peritoneal drainage tubes can thus be formed that are more tolerable to the patient. These and similar sources of abdominal pain are thus addressed according to the invention.

Similar drainage or drug introduction tubes associated with the head and neck or the vascular system can be constructed according to the invention. For intestinal applications, in addition to the naso-gastric tube, there are situations in which long tubes are used to decompress the bowel. Such tubes pass through the nose and are carried into the bowel to a point of obstruction to carry excretions away. Such entubation is extremely uncomfortable for the patient. Safety of such procedures as well as patient tolerance can be readily improved with the methods and compositions of the present invention.

Other embodiments of the invention will occur to those skilled in the art.

In some cases the anesthetic base, such as lidocaine, may be dissolved in a biocompatible polymer, or in another polymer covered with a biocompatible polymer, as an implant for timed release of e.g. lidocaine as a long-term antiarrythmia medication.

What is claimed is:

1. A flexible tube for introduction into a body passage of an animal for medical purposes, said tube having a wall with an inner surface defining an interior lumen, the wall having an outward facing surface which, when the tube is emplaced in a body passage of an animal, contacts body tissue of the animal, the wall of said tube being composed of wall material having dissolved therein a topical anesthetic compound, the topical anesthetic compound being more soluble in the wall material than in water, the concentration of anesthetic compound in the wall material being such that it contributes as plasticizer to render the wall material flexible to a predetermined desired degree while being in concentration such that when the tube is emplaced in and in contact with an animal's body passage, anesthetic compound diffuses to a surface of the body passage in contact with the tube at a rate to be effective in maintaining anesthesia.

2. The tube of claim 1 in the form of an endotracheal tube, to which an inflatable cuff is affixed.

3. The tube of claim 2 wherein said inflatable cuff is comprised of a thin wall material having dissolved therein a topical anesthetic compound that is more soluble in the wall material than in water.

4. The tube of claim 1 in the form of tube placeable into the body through the nose.

5. The tube of claim 4 in which said tube is a naso-gastric feeding tube.

6. The tube of claim 1 in the form of a drainage tube having drainage entry holes along a portion of the tube.

7. The tube of claim 6 in the form of a drainage tube constructed to lie in the posterior gutter along the spine.

8. The tube of claim 1 wherein said tube is constructed to pass through the abdominal wall.

9. The tube of claim 8 wherein said tube is constructed to cross the peritoneum and pass through the stomach wall.

10. The tube of claim 1 wherein said tube is a Foley catheter.

11. The tube of claim 10 in which a balloon on said Foley catheter is comprised of a thin wall material having dissolved therein a topical anesthetic compound that is more soluble in the wall material than in water.

12. The tube of claim 1 wherein a superficial portion of topical anesthetic on said tube is of water soluble form.

13. The tube of claim 1 wherein said tube is resin of extruded form, said topical anesthetic being present in solution in said resin throughout the thickness of said extruded form.

14. The tube of claim 1 wherein the concentration of said anesthetic is greater in the material of said tube near said outward facing surface than the concentration deeper therein.

15. A tube as claimed in claim 1, wherein said topical anesthetic compound is unreactive with ethylene oxide as used in sterilizing procedures.

16. A tube as claimed in claim 1, wherein said wall material comprises polyvinyl chloride.

17. A tube as claimed in claim 1, wherein said wall material comprises vinyl-urethane copolymer.

18. A tube as claimed in claim 1, wherein said topical anesthetic compound is lidocaine base.

19. A tube as claimed in claim 1, wherein said topical anesthetic compound is dibucaine base.

20. A tube as claimed in claim 1, wherein said topical anesthetic compound is prilocaine base.

21. An insertable medical device for introduction into a body of an animal for medical purposes, comprising a polymeric structure exposed for contact with body fluid or tissue of said animal, said polymeric structure comprising a plasticizable resin, said resin including a predetermined desired quantity of plasticizer chosen to determine a predetermined flexibility characteristic for said resin, said plasticizer quantity being comprised of at least about 25% topical anesthetic base soluble in said resin, said topical anesthetic base being more soluble in said resin than in water, the concentration and character of said anesthetic in the resin being such that when the medical device is emplaced in and in contact with the animal's body fluid or tissue, anesthetic compound diffuses to a surface of said polymeric structure and to said fluid or tissue in contact with said structure at a rate to be effective to provide a desired dosage.

22. The medical device of claim 21 wherein said polymeric structure comprises a tube having a wall defining an interior lumen, the wall having an outward facing surface which, when the tube is emplaced in a body passage of an animal, contacts body tissue of the animal, the wall of said tube being comprised of wall material having dissolved therein said topical anesthetic base.

23. A medical device as claimed in claim 21, wherein said plasticizable resin comprises polyvinyl chloride.

24. A medical device as claimed in claim 21, wherein said plasticizable resin comprises a polyvinyl copolymer.

25. A medical device as claimed in claim 21, wherein said topical anesthetic base comprises lidocaine.

26. A medical device as claimed in claim 21, wherein said topical anesthetic base comprises dibucaine.

27. A medical device as claimed in claim 21, wherein said topical anesthetic base comprises prilocaine.

28. A medical device as claimed in 27, wherein said topical anesthetic base further comprises lidocaine.

29. An insertable medical device comprising a structure having an inflatable member, said inflatable member comprising a thin, flexible wall of polymeric resin, at least an outer portion of said thin, flexible wall having dissolved in said resin a topical anesthetic base that is characterized by being more soluble in said resin than in water.

30. The inflatable member of claim 29 wherein said inflatable member comprises a cuff for an endotracheal tube.

31. The inflatable member of claim 29 in the form of an inflatable sleeve extending along the length of a medical tube.

32. The inflatable member of claim 31 in the form of a balloon of a Foley catheter.

33. The medical device of claim 21 or 29 wherein said structure comprises multiple coextruded layers of polymeric resin, at least one of said layers having said anesthetic base dissolved therein.

34. An insertable medical device comprising a polymeric structure having multiple coextruded layers of polymeric resin, at least one of said layers having dissolved therein a topical anesthetic base that is characterized by being more soluble in the constituent resin than in water.

35. The medical device of claim 34 wherein a further layer on one side of said layer in which said anesthetic is dissolved is a barrier layer comprised of a polymeric resin in which said anesthetic base is not as soluble as it is in said layer in which said anesthetic is dissolved.

36. The medical device of claim 35 wherein said barrier layer is comprised of polyethylene.

37. A medical device for introduction into a body of an animal for medical purposes, said medical device having a wall structure having an outward facing surface which, when the device is emplaced in a body of an animal, contacts body fluid or tissue of the animal, the wall of said device being composed of material having dissolved therein a topical anesthetic compound, the topical anesthetic compound being more soluble in the material than in water, and wherein the material of said wall structure below said outward facing surface comprises polymer having dissolved therein said topical anesthetic compound that is more soluble in said polymer than in water and material of said device at said outward facing surface contains a water-soluble form of anesthetic comprising a reaction product of an anesthetic in base form.

38. A medical device according to claim 37 wherein said water soluble form of anesthetic is a hydrochloride of said anesthetic.

39. An insertable medical device for introduction into a body of an animal for medical purposes, comprising a polymeric structure exposed for contact with body fluid or tissue of said animal, said polymeric structure comprising a plasticizable resin, said resin including a predetermined quantity of plasticizer chosen to determine a predetermined durometer characteristic of said resin, at least part of said plasticizer being at least one topical anesthetic compound that has plasticizer properties and is more soluble in said resin than in water, the concentration of anesthetic compound in said resin being such that when the medical device is emplaced in and in contact with an animal's body tissue or fluid, anesthetic compound diffuses to a surface of the device and into said tissue or fluid at a rate to be effective to provide a desired dosage.

40. The medical device of claim 39, wherein the plasticizer present comprises two or more plasticizers, one of which has the characteristic of enhancing the diffusion rate through said resin of a said anesthetic compound.

41. The medical device as claimed in claim 40, wherein said anesthetic base is lidocaine and at least 25% of the plasticizer is diisooctylpthalate.

42. The medical device as claimed in claim 40 wherein at least 25% of said plasticizer present is topical anesthetic base.

43. The medical device as claimed in claim 39, wherein substantially all of said plasticizer is comprised of one or more topical anesthetic bases.

44. An insertable medical article constructed to administer anesthetic within a body comprising a polymeric structure formed of a plasticizable resin, said resin containing a quantity of plasticizer dissolved in said resin, wherein a substantial part of said plasticizer dissolved in said resin is topical anesthetic base that is more soluble in said resin than in water.

45. A medical device for introduction into body of an animal for medical purposes, said medical device comprising a plasticizable resin endotracheal tube shaft which, when the tube shaft is emplaced in a body of an animal, contacts body fluid or tissue of the animal, the tube shaft comprising a topical anesthetic base dissolved in said resin, the topical anesthetic compound being more soluble in said resin than in water, the concentration of anesthetic compound in the resin being such that when the tube shaft is emplaced in and in contact with the animal's body fluid or tissue, anesthetic compound diffuses to a surface of the tube shaft in contact with the body fluid or tissue at a rate to be effective in maintaining anesthesia.

46. A medical device for introduction into a body of an animal for medical purposes, said medical device comprising a plasticizable resin inflatable endotracheal tube cuff which, when the tube cuff is emplaced in a body of an animal, contacts body fluid or tissue of the animal, the tube cuff comprising a topical anesthetic base dissolved in said resin, the topical anesthetic compound being more soluble in said resin than in water, the concentration of anesthetic compound in the resin being such that when the tube cuff is emplaced in and in contact with the animal's body fluid or tissue, anesthetic compound diffuses to a surface of the tube cuff in contact with the body fluid or tissue at a rate to be effective in maintaining anesthesia.

47. A medical device for introduction into a body of an animal for medical purposes, said medical device comprising a plasticizable resin endotracheal tube comprising a shaft and inflatable cuff which, when the endotracheal tube is emplaced in a body of an animal, contacts body fluid or tissue of the animal, said shaft and said inflatable cuff each comprising a topical anesthetic base dissolved in said resin and wherein the concentration of said topical anesthetic base dissolved in said resin in an exposed surface of said shaft is less than the concentration of said topical anesthetic base dissolved in said resin in an exposed surface of said cuff, the topical anesthetic compound being more soluble in said resin than in water and diffusing to body fluid or tissue of the animal at a rate to be effective in maintaining anesthesia.

48. An insertable device for introduction into a body passage of an animal for medical purposes, said device being at least partially covered with a relatively loose-fitting plasticizable resin film which, when the device is emplaced in a body of an animal, contacts body fluid or tissue of the animal, the film comprising a topical anesthetic base dissolved in the resin of the film, the topical anesthetic compound being more soluble in said resin than in water, the concentration of anesthetic compound in the resin being such that when the device is emplaced in the animal and the film is in contact with the animal's body fluid or tissue, anesthetic compound diffuses to a surface of the film in contact with the body fluid or tissue at a rate to be effective in maintaining anesthesia.

* * * * *

UNITED STATES PATENT AND TRADEMARK OFFICE
CERTIFICATE OF CORRECTION

PATENT NO.   : 5,417,671

DATED        : May 23, 1995

INVENTOR(S)  : Richard R. Jackson

It is certified that error appears in the above-identified patent and that said Letters Patent is hereby corrected as shown below:

On the title page, item [56], under "References Cited, U.S. PATENT DOCUMENTS", the following references should be added:

| | |
|---|---|
| 3,638,655 | Doherty |
| 4,421,333 | Greco et al. |
| 4,560,720 | Adyogi et al. |
| 4,581,028 | Fox, Jr. et al. |
| 4,867,968 | Allen |
| 4,879,135 | Greco et al. |
| 4,917,686 | Bayston et al. |
| 4,977,894 | Davies |
| 4,997,440 | Dumican |

Col. 16, line 61 - "enhances" should be --enhance--.

Signed and Sealed this

Tenth Day of September, 1996

Attest:

BRUCE LEHMAN

*Attesting Officer*   *Commissioner of Patents and Trademarks*